(12) United States Patent
Maile et al.

(10) Patent No.: US 11,116,988 B2
(45) Date of Patent: Sep. 14, 2021

(54) IMPLANTABLE MEDICAL DEVICE WITH RECHARGEABLE BATTERY

(71) Applicant: CARDIAC PACEMAKERS, INC., St. Paul, MN (US)

(72) Inventors: Keith R. Maile, New Brighton, MN (US); Michael J. Kane, St. Paul, MN (US); William J. Linder, Golden Valley, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 176 days.

(21) Appl. No.: 15/475,918

(22) Filed: Mar. 31, 2017

(65) Prior Publication Data
US 2017/0281955 A1    Oct. 5, 2017

Related U.S. Application Data

(60) Provisional application No. 62/316,158, filed on Mar. 31, 2016.

(51) Int. Cl.
*A61N 1/378* (2006.01)
*A61N 1/372* (2006.01)
(Continued)

(52) U.S. Cl.
CPC ............ *A61N 1/3787* (2013.01); *A61B 5/287* (2021.01); *A61B 5/686* (2013.01); *A61N 1/056* (2013.01);
(Continued)

(58) Field of Classification Search
CPC ........ A61N 1/3787; A61N 1/056; A61N 1/37; A61N 1/37205; A61N 1/3756; A61N 1/37229; A61B 5/0422; A61B 5/686
(Continued)

(56) References Cited

U.S. PATENT DOCUMENTS 3,835,864 A    9/1974  Rasor et al.
3,943,936 A    3/1976  Rasor et al.
(Continued)

FOREIGN PATENT DOCUMENTS

AU    2008279789 B2    10/2011
AU    2008329620 B2    5/2014
(Continued)

OTHER PUBLICATIONS

US 8,886,318 B2, 11/2014, Jacobson et al. (withdrawn)
(Continued)

*Primary Examiner* — Niketa I Patel
*Assistant Examiner* — Minh Duc G Pham
(74) *Attorney, Agent, or Firm* — Seager, Tufte & Wickhem LLP.

(57) ABSTRACT

Implantable medical devices such as leadless cardiac pacemakers may include a rechargeable power source. In some cases, a system may include an implanted device including a receiving antenna and an external transmitter that transmits radiofrequency energy that may be captured by the receiving antenna and then be converted into electrical energy that may be used to recharge a rechargeable power source. Accordingly, since the rechargeable power source does not have to maintain sufficient energy stores for the expected life of the implanted device, the power source itself and thus the implanted device, may be made smaller while still meeting device longevity expectations.

18 Claims, 14 Drawing Sheets

(51) Int. Cl.
*A61B 5/287* (2021.01)
*A61B 5/00* (2006.01)
*A61N 1/05* (2006.01)
*A61N 1/37* (2006.01)
*A61N 1/375* (2006.01)

(52) U.S. Cl.
CPC ............ *A61N 1/37* (2013.01); *A61N 1/3756* (2013.01); *A61N 1/37205* (2013.01); *A61B 2560/0219* (2013.01); *A61N 1/37229* (2013.01)

(58) Field of Classification Search
USPC .......................................................... 607/5
See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,457 A | 5/1994 | Jeutter et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |

(56) References Cited

U.S. PATENT DOCUMENTS

| | | |
|---|---|---|
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Colson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,456,256 B1 * | 9/2002 | Amundson ........ A61N 1/37229 128/903 |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |

(56) References Cited

U.S. PATENT DOCUMENTS

| | | |
|---|---|---|
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |

(56) References Cited

U.S. PATENT DOCUMENTS

| | | |
|---|---|---|
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bomzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |

(56) References Cited

U.S. PATENT DOCUMENTS

| | | |
|---|---|---|
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishier et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |

(56) References Cited

U.S. PATENT DOCUMENTS

| | | |
|---|---|---|
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0206170 A1* | 9/2006 | Denker .................. H01Q 21/24 607/60 |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150019 A1 | 6/2007 | Youker et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |

(56) References Cited

U.S. PATENT DOCUMENTS

| | | |
|---|---|---|
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0276111 A1 | 11/2011 | Carbunaru et al. |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Mates |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1* | 3/2014 | Khairkhahan ......... A61N 1/362 606/129 |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |

(56) References Cited

U.S. PATENT DOCUMENTS

| | | |
|---|---|---|
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0097734 A1* | 4/2015 | Zhao ............... A61N 1/37229 343/702 |
| 2015/0100108 A1 | 4/2015 | Vansickle et al. |
| 2015/0105836 A1 | 4/2015 | Bonner et al. |
| 2015/0127068 A1* | 5/2015 | Simon ............... A61N 1/36153 607/60 |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0231398 A1* | 8/2015 | Marnfeldt ............ H02J 7/0024 607/61 |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2018/0228397 A1* | 8/2018 | Dumanli Oktar ...... A61B 5/076 |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 603823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 6199867 B2 | 2/2013 |
| WO | 09500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006045075 A1 | 4/2006 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, Jan. 29, 2016, 15 pages.

Spickler et al., "Totally Self-Contained Intracardiac Pacemaker," Journal of Electrocardiology, vol. 3(384): 324-331, 1970.

"Instructions for Use System 1, Leadless Cardiac Pacemaker (LCP) and Delivery Catheter," Nanostim Leadless Pacemakers, pp. 1-28, 2013.

International Search Report and Written Opinion for Application No. PCT/US20171025384, 24 pages, dated Jun. 28, 2017.

\* cited by examiner

IMPLANTABLE MEDICAL DEVICE WITH RECHARGEABLE BATTERY

CROSS REFERENCE TO RELATED APPLICATIONS

This application claims the benefit of U.S. Provisional Patent Application Ser. No. 62/316,158 filed on Mar. 31, 2016, the disclosure of which is incorporated herein by reference.

TECHNICAL FIELD

The disclosure relates generally to implantable medical devices, and more particularly to implantable medical devices that have a power source that may be wirelessly recharged from a remote location.

BACKGROUND

Cardiac pacemakers such as leadless cardiac pacemakers are used to sense and pace hearts that are susceptible to a variety of incorrect heart rhythms, including but not limited to bradycardia, which is a slow heart rate, and tachycardia, which is a high heart rate. In many leadless cardiac pacemakers, due to their relatively small size, a relatively large fraction of the internal space of the leadless cardiac pacemaker is consumed by a battery. As the battery life determines the potential useful life expectancy of the leadless cardiac pacemaker, there is a desire to make the batteries as large as possible within the confines of the available space.

What would be desirable is an implantable medical device that has a long useful life expectancy while not requiring as much battery space, thereby permitting a significantly smaller device size. A smaller device size may make the device more easily deliverable and implantable in the body, allow the device to be implantable in smaller and more confined spaces in the body, and/or may make the device less expensive to produce.

SUMMARY

The disclosure is directed to implantable medical that provide a long lasting power source within a smaller device housing. While a leadless cardiac pacemaker is used as an example implantable medical device, the disclosure may be applied to any suitable implantable medical device including, for example, neuro-stimulators, diagnostic devices including those that do not deliver therapy, and/or any other suitable implantable medical device as desired.

In some cases, the disclosure pertains to implantable medical devices such as leadless cardiac pacemakers that include a rechargeable power source such as a rechargeable battery, a rechargeable capacitor or a rechargeable supercapacitor. In some cases, a system may include an implanted device including a receiving antenna and an external transmitter that transmits radiofrequency energy that may be captured by the receiving antenna and then converted into electrical energy that may be used to recharge the rechargeable power source. Accordingly, since the rechargeable power source does not have to maintain sufficient energy stores in a single charge for the entire expected life of the implanted device, the power source itself and thus the implanted device, may be made smaller while still meeting device longevity expectations.

In an example of the disclosure, an implantable medical device (IMD) that is configured to be implanted within a patient includes a housing configured for trans-catheter deployment and a plurality of electrodes that are exposed external to the housing. Therapeutic circuitry is disposed within the housing and may be operatively coupled to the plurality of electrodes and configured to sense one or more signals via one or more of the plurality of electrodes and/or to stimulate tissue via one or more of the plurality of electrodes. A rechargeable power source may be disposed within the housing and may be configured to power the therapeutic circuitry. A receiving antenna may be disposed relative to the housing and may be configured to receive transmitted radiative Electro-Magnetic (EM) energy through the patient's body. Charging circuitry may be operably coupled with the receiving antenna and the rechargeable power source and may be configured to use the radiative EM energy received via the receiving antenna to charge the rechargeable power source.

Alternatively or additionally to any of the embodiments above, the IMD may also include a secondary battery disposed within the housing and operatively coupled to the therapeutic circuitry, the secondary battery functioning as a backup battery to the rechargeable power source.

Alternatively or additionally to any of the embodiments above, the secondary battery is a non-rechargeable battery.

Alternatively or additionally to any of the embodiments above, the IMD is a leadless cardiac pacemaker (LCP).

Alternatively or additionally to any of the embodiments above, the housing is substantially transparent to radiative EM energy.

Alternatively or additionally to any of the embodiments above, the housing may include a ceramic housing, a glass housing, or a polymeric housing.

Alternatively or additionally to any of the embodiments above, the receiving antenna may include a first metal pattern formed on an outer surface of a sleeve insert and a second metal pattern formed on an inner surface of the sleeve insert, and the sleeve insert is configured to be inserted into an elongated cavity of the housing of the IMD.

Alternatively or additionally to any of the embodiments above, the receiving antenna may include a first metal pattern formed on an outer surface of an outer sleeve and a second metal pattern formed on an inner surface of the outer sleeve, and the outer sleeve is configured to fit over and be secured relative to the housing of the IMD.

Alternatively or additionally to any of the embodiments above, at least one of the plurality of electrodes forms part of the receiving antenna.

In another example of the disclosure, an implantable medical device (IMD) configured to be implanted within a patient includes a housing that is substantially transparent to radiative Electro-Magnetic (EM) energy along at least part of its length and circuitry that is disposed within the housing. A plurality of electrodes may be exposed external to the housing and operatively coupled to the circuitry. A rechargeable power source may be disposed within the housing and may be configured to power the IMD including the circuitry. A receiving antenna may be disposed within the housing and may be configured to receive transmitted radiative EM energy through the at least part of the housing that is substantially transparent to radiative EM energy. The circuit may be operably coupled with the receiving antenna and the rechargeable power source and be configured to use the radiative EM energy received via the receiving antenna to charge the rechargeable power source.

Alternatively or additionally to any of the embodiments above, the IMD is a leadless cardiac pacemaker (LCP).

Alternatively or additionally to any of the embodiments above, the IMD is an implantable monitoring device.

Alternatively or additionally to any of the embodiments above, the IMD is an implantable sensor.

Alternatively or additionally to any of the embodiments above, the receiving antenna may include a first receiving antenna having a first null and a second receiving antenna having a second null offset from the first null.

Alternatively or additionally to any of the embodiments above, the housing may include ceramic.

Alternatively or additionally to any of the embodiments above, the housing may include glass.

Alternatively or additionally to any of the embodiments above, the receiving antenna may be configured to receive sufficient radiative EM energy from a wavelength band of radiative EM energy transmitted from outside the patient to recharge the rechargeable power source at a rate faster than the rechargeable power source is depleted by powering the IMD when the wavelength band of radiative EM energy is transmitted at an intensity that does not cause heat damage to the patient.

Alternatively or additionally to any of the embodiments above, at least a portion of the housing has a substantially cylindrical profile and the receiving antenna includes a planar antenna that has been conformed to the substantially cylindrical profile.

In another example of the disclosure, an implantable medical device (IMD) configured to be implanted within a patient includes a housing forming at least part of a receiving antenna, wherein the receiving antenna is configured to receive transmitted radiative Electro-Magnetic (EM) energy through the patient's body. A plurality of electrodes may be exposed external to the housing and circuitry may be disposed within the housing. The circuitry may be operatively coupled to the plurality of electrodes and may be configured to sense one or more signals via one or more of the plurality of electrodes and/or may stimulate tissue via one or more of the plurality of electrodes. A rechargeable power source may be disposed within the housing and may be configured to power the circuitry. Charging circuitry may be operably coupled with the receiving antenna and the rechargeable power source and may be configured to use the radiative EM energy received via the receiving antenna to charge the rechargeable power source.

Alternatively or additionally to any of the embodiments above, the housing may form one or more layers of the receiving antenna.

The above summary of some illustrative embodiments is not intended to describe each disclosed embodiment or every implementation of the present disclosure. The Figures and Description which follow more particularly exemplify these and other illustrative embodiments.

BRIEF DESCRIPTION OF THE FIGURES

The disclosure may be more completely understood in consideration of the following description in connection with the accompanying drawings, in which.

Figure 1:
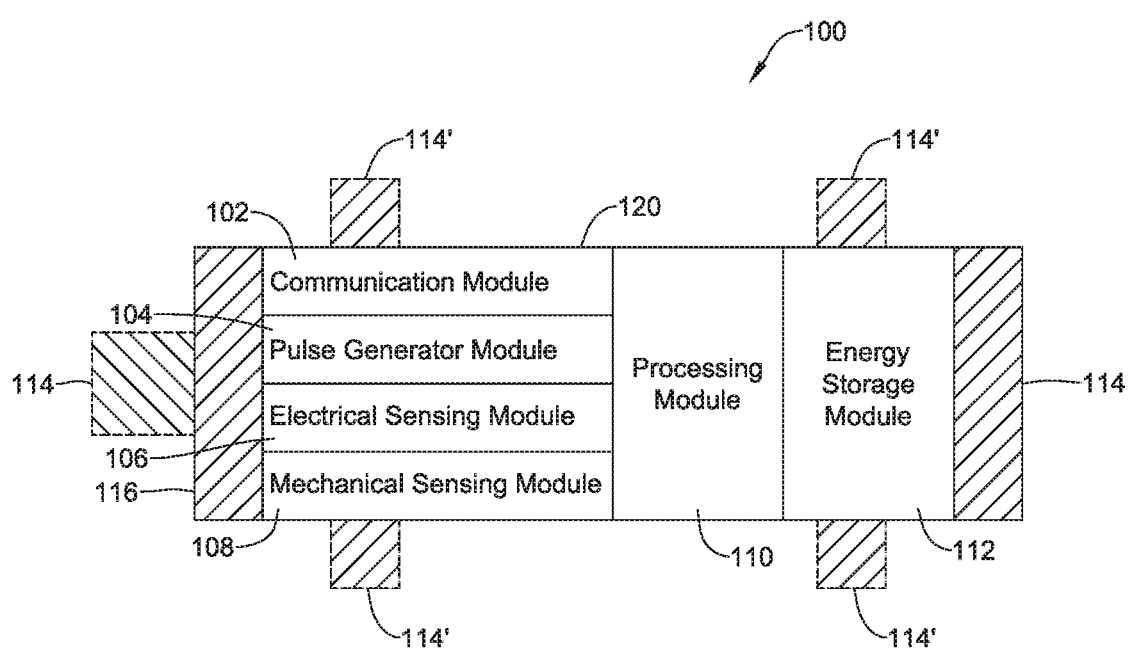
FIG. 1 is a schematic block diagram of an illustrative leadless cardiac pacemaker (LCP)

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure.

FIG. 1 is a conceptual schematic block diagram of an illustrative leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, the LCP 100 may be a compact device with all components housed within the LCP 100 or directly on a housing 120. In some instances, the LCP 100 may include one or more of a communication module 102, a pulse generator module 104, an electrical sensing module 106, a mechanical sensing module 108, a processing module 110, an energy storage module 112, and electrodes 114.

As depicted in FIG. 1, the LCP 100 may include electrodes 114, which can be secured relative to the housing 120 and electrically exposed to tissue and/or blood surrounding the LCP 100. The electrodes 114 may generally conduct electrical signals to and from the LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

The electrodes 114 may include one or more biocompatible conductive materials such as various metals or alloys that are known to be safe for implantation within a human body. In some instances, the electrodes 114 may be generally disposed on either end of the LCP 100 and may be in electrical communication with one or more of modules the 102, 104, 106, 108, and 110. In embodiments where the electrodes 114 are secured directly to the housing 120, an insulative material may electrically isolate the electrodes 114 from adjacent electrodes, the housing 120, and/or other parts of the LCP 100. In some instances, some or all of the electrodes 114 may be spaced from the housing 120 and may be connected to the housing 120 and/or other components of the LCP 100 through connecting wires. In such instances, the electrodes 114 may be placed on a tail (not shown) that extends out away from the housing 120. As shown in FIG. 1, in some embodiments, the LCP 100 may include electrodes 114'. The electrodes 114' may be in addition to the electrodes 114, or may replace one or more of the electrodes 114. The electrodes 114' may be similar to the electrodes 114 except that the electrodes 114' are disposed on the sides of the LCP 100. In some cases, the electrodes 114' may increase the number of electrodes by which the LCP 100 may deliver communication signals and/or electrical stimulation pulses, and/or may sense intrinsic cardiac electrical signals, communication signals, and/or electrical stimulation pulses.

The electrodes 114 and/or 114' may assume any of a variety of sizes and/or shapes, and may be spaced at any of a variety of spacings. For example, the electrodes 114 may have an outer diameter of two to twenty millimeters (mm). In other embodiments, the electrodes 114 and/or 114' may have a diameter of two, three, five, seven millimeters (mm), or any other suitable diameter, dimension and/or shape. Example lengths for the electrodes 114 and/or 114' may include, for example, one, three, five, ten millimeters (mm), or any other suitable length. As used herein, the length is a dimension of the electrodes 114 and/or 114' that extends away from the outer surface of the housing 120. In some instances, at least some of the electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, the communication module 102 may be electrically coupled to the electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. The communication module 102 may additionally be configured to sense for communication signals delivered by other devices, which may be located external or internal to the patient's body.

The communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, the LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. In some cases, processed information may, for example, be provided by a chemical sensor or an optically interfaced sensor. Messages and/or commands may include instructions or the like directing another device to take action, notifications of imminent actions of the sending device, requests for reading from the receiving device, requests for writing data to the receiving device, information messages, and/or other messages commands.

In at least some embodiments, the communication module 102 (or the LCP 100) may further include switching circuitry to selectively connect one or more of the electrodes 114 and/or 114' to the communication module 102 in order to select which of the electrodes 114 and/or 114' that the communication module 102 delivers communication pulses with. It is contemplated that the communication module 102 may be communicating with other devices via conducted signals, radio frequency (RF) signals, optical signals, acoustic signals, inductive coupling, and/or any other suitable communication methodology. Where the communication module 102 generates electrical communication signals, the communication module 102 may include one or more capacitor elements and/or other charge storage devices to aid in generating and delivering communication signals. In the embodiment shown, the communication module 102 may use energy stored in the energy storage module 112 to generate the communication signals. In at least some examples, the communication module 102 may include a switching circuit that is connected to the energy storage module 112 and, with the switching circuitry, may connect the energy storage module 112 to one or more of the electrodes 114/114' to generate the communication signals.

As shown in FIG. 1, a pulse generator module 104 may be electrically connected to one or more of the electrodes 114 and/or 114'. The pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, the LCP 100 may vary the rate at which the pulse generator module 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like. The pulse generator module 104 may include one or more capacitor elements and/or other charge storage devices to aid in generating and delivering appropriate electrical stimulation pulses. In at least some embodiments, the pulse generator module 104 may use energy stored in the energy storage module 112 to generate the electrical stimulation pulses. In some particular embodiments, the pulse generator module 104 may include a switching circuit that is connected to the energy storage module 112 and may connect the energy storage module 112 to one or more of the electrodes 114/114' to generate electrical stimulation pulses.

The LCP 100 may further include an electrical sensing module 106 and a mechanical sensing module 108. The electrical sensing module 106 may be configured to sense intrinsic cardiac electrical signals conducted from the electrodes 114 and/or 114' to the electrical sensing module 106. For example, the electrical sensing module 106 may be electrically connected to one or more of the electrodes 114 and/or 114' and the electrical sensing module 106 may be configured to receive cardiac electrical signals conducted through the electrodes 114 and/or 114' via a sensor amplifier or the like. In some embodiments, the cardiac electrical signals may represent local information from the chamber in which the LCP 100 is implanted. For instance, if the LCP 100 is implanted within a ventricle of the heart, cardiac electrical signals sensed by the LCP 100 through the electrodes 114 and/or 114' may represent ventricular cardiac electrical signals. The mechanical sensing module 108 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. The electrical sensing module 106 and the mechanical sensing module 108 may both be connected to the processing module 110 and may provide signals representative of the sensed cardiac electrical signals and/or physiological signals to the processing module 110. Although described with respect to FIG. 1 as separate sensing modules, in some embodiments, the electrical sensing module 106 and the mechanical sensing module 108 may be combined into a single module. In at least some examples, the LCP 100 may only include one of the electrical sensing module 106 and the mechanical sensing module 108. In some cases, any combination of the processing module 110, the electrical sensing module 106, the mechanical sensing module 108, the communication module 102, the pulse generator module 104 and/or the energy storage module may be considered a controller of the LCP 100.

The processing module 110 may be configured to direct the operation of the LCP 100 and may, in some embodiments, be termed a controller. For example, the processing module 110 may be configured to receive cardiac electrical signals from the electrical sensing module 106 and/or physiological signals from the mechanical sensing module 108. Based on the received signals, the processing module 110 may determine, for example, occurrences and types of arrhythmias and other determinations such as whether the LCP 100 has become dislodged. The processing module 110 may further receive information from the communication module 102. In some embodiments, the processing module 110 may additionally use such received information to determine occurrences and types of arrhythmias and/or and other determinations such as whether the LCP 100 has become dislodged. In still some additional embodiments, the LCP 100 may use the received information instead of the signals received from the electrical sensing module 106 and/or the mechanical sensing module 108—for instance if the received information is deemed to be more accurate than the signals received from the electrical sensing module 106 and/or the mechanical sensing module 108 or if the electrical sensing module 106 and/or the mechanical sensing module 108 have been disabled or omitted from the LCP 100.

After determining an occurrence of an arrhythmia, the processing module 110 may control the pulse generator module 104 to generate electrical stimulation pulses in accordance with one or more electrical stimulation therapies to treat the determined arrhythmia. For example, the processing module 110 may control the pulse generator module 104 to generate pacing pulses with varying parameters and in different sequences to effectuate one or more electrical stimulation therapies. As one example, in controlling the pulse generator module 104 to deliver bradycardia pacing therapy, the processing module 110 may control the pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, the processing module 110 may monitor one or more physiological parameters of the patient which may indicate a need for an increased heart rate (e.g. due to increased metabolic demand). The processing module 110 may then increase the rate at which the pulse generator module 104 generates electrical stimulation pulses. Adjusting the rate of delivery of the electrical stimulation pulses based on the one or more physiological parameters may extend the battery life of the LCP 100 by only requiring higher rates of delivery of electrical stimulation pulses when the physiological parameters indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

For ATP therapy, the processing module 110 may control the pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, the processing module 110 may control the pulse generator module 104 to reduce the rate of delivered pacing pulses down to a safer level. In CRT, the processing module 110 may control the pulse generator module 104 to deliver pacing pulses in coordination with another device to cause the heart to contract more efficiently. In cases where the pulse generator module 104 is capable of generating defibrillation and/or cardioversion pulses for defibrillation/cardioversion therapy, the processing module 110 may control the pulse generator module 104 to generate such defibrillation and/or cardioversion pulses. In some cases, the processing module 110 may control the pulse generator module 104 to generate electrical stimulation pulses to provide electrical stimulation therapies different than those examples described above.

Aside from controlling the pulse generator module 104 to generate different types of electrical stimulation pulses and in different sequences, in some embodiments, the processing module 110 may also control the pulse generator module 104 to generate the various electrical stimulation pulses with varying pulse parameters. For example, each electrical stimulation pulse may have a pulse width and a pulse amplitude. The processing module 110 may control the pulse generator module 104 to generate the various electrical stimulation pulses with specific pulse widths and pulse amplitudes. For example, the processing module 110 may cause the pulse generator module 104 to adjust the pulse width and/or the pulse amplitude of electrical stimulation pulses if the electrical stimulation pulses are not effectively capturing the heart. Such control of the specific parameters of the various electrical stimulation pulses may help the LCP 100 provide more effective delivery of electrical stimulation therapy.

In some embodiments, the processing module 110 may further control the communication module 102 to send information to other devices. For example, the processing module 110 may control the communication module 102 to generate one or more communication signals for communicating with other devices of a system of devices. For instance, the processing module 110 may control the communication module 102 to generate communication signals in particular pulse sequences, where the specific sequences convey different information. The communication module 102 may also receive communication signals for potential action by the processing module 110.

In further embodiments, the processing module 110 may control switching circuitry by which the communication module 102 and the pulse generator module 104 deliver communication signals and/or electrical stimulation pulses to tissue of the patient. As described above, both the communication module 102 and the pulse generator module 104 may include circuitry for connecting one or more of the electrodes 114 and/or 114' to the communication module 102 and/or the pulse generator module 104 so those modules may deliver the communication signals and electrical stimulation pulses to tissue of the patient. The specific combination of one or more electrodes by which the communication module 102 and/or the pulse generator module 104 deliver communication signals and electrical stimulation pulses may influence the reception of communication signals and/or the effectiveness of electrical stimulation pulses. Although it was described that each of the communication module 102 and the pulse generator module 104 may include switching circuitry, in some embodiments, the LCP 100 may have a single switching module connected to the communication module 102, the pulse generator module 104, and the electrodes 114 and/or 114'. In such embodiments, processing module 110 may control the switching module to connect the modules 102/104 and the electrodes 114/114' as appropriate.

In some embodiments, the processing module 110 may include a pre-programmed chip, such as a very-large-scale integration (VLSI) chip or an application specific integrated circuit (ASIC). In such embodiments, the chip may be pre-programmed with control logic in order to control the operation of the LCP 100. By using a pre-programmed chip, the processing module 110 may use less power than other programmable circuits while able to maintain basic functionality, thereby potentially increasing the battery life of the LCP 100. In other instances, the processing module 110 may include a programmable microprocessor or the like. Such a programmable microprocessor may allow a user to adjust the control logic of the LCP 100 after manufacture, thereby allowing for greater flexibility of the LCP 100 than when using a pre-programmed chip. In still other embodiments, the processing module 110 may not be a single component. For example, the processing module 110 may include multiple components positioned at disparate locations within the LCP 100 in order to perform the various described functions. For example, certain functions may be performed in one component of the processing module 110, while other functions are performed in a separate component of the processing module 110.

The processing module 110, in additional embodiments, may include a memory circuit and the processing module 110 may store information on and read information from the memory circuit. In other embodiments, the LCP 100 may include a separate memory circuit (not shown) that is in communication with the processing module 110, such that the processing module 110 may read and write information to and from the separate memory circuit. The memory circuit, whether part of the processing module 110 or separate from the processing module 110, may be volatile memory, non-volatile memory, or a combination of volatile memory and non-volatile memory.

The energy storage module 112 may provide a power source to the LCP 100 for its operations. In some embodiments, the energy storage module 112 may be a non-rechargeable lithium-based battery. In other embodiments, the non-rechargeable battery may be made from other suitable materials. In some embodiments, the energy storage module 112 may be considered to be a rechargeable power supply, such as but not limited to, a rechargeable battery. In still other embodiments, the energy storage module 112 may include other types of energy storage devices such as capacitors or super capacitors. In some cases, as will be discussed, the energy storage module 112 may include a rechargeable primary battery and a non-rechargeable secondary battery. In some cases, the primary battery and the second battery, if present, may both be rechargeable.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, the anchor 116 may include other structures such as barbs, spikes, or the like to facilitate engagement with the surrounding cardiac tissue.

In some examples, the LCP 100 may be configured to be implanted on a patient's heart or within a chamber of the patient's heart. For instance, the LCP 100 may be implanted within any of a left atrium, right atrium, left ventricle, or right ventricle of a patient's heart. By being implanted within a specific chamber, the LCP 100 may be able to sense cardiac electrical signals originating or emanating from the specific chamber that other devices may not be able to sense with such resolution. Where the LCP 100 is configured to be implanted on a patient's heart, the LCP 100 may be configured to be implanted on or adjacent to one of the chambers of the heart, or on or adjacent to a path along which intrinsically generated cardiac electrical signals generally follow. In these examples, the LCP 100 may also have an enhanced ability to sense localized intrinsic cardiac electrical signals and deliver localized electrical stimulation therapy. In embodiments where the LCP 100 includes an accelerometer, the LCP 100 may additionally be able to sense the motion of the cardiac wall to which the LCP 100 is attached.

While a leadless cardiac pacemaker is used as an example implantable medical device in FIG. 1, the disclosure may be applied to any suitable implantable medical device including, for example, neuro-stimulators, diagnostic devices including those that do not deliver therapy, and/or any other suitable implantable medical device as desired.

Figure 2:
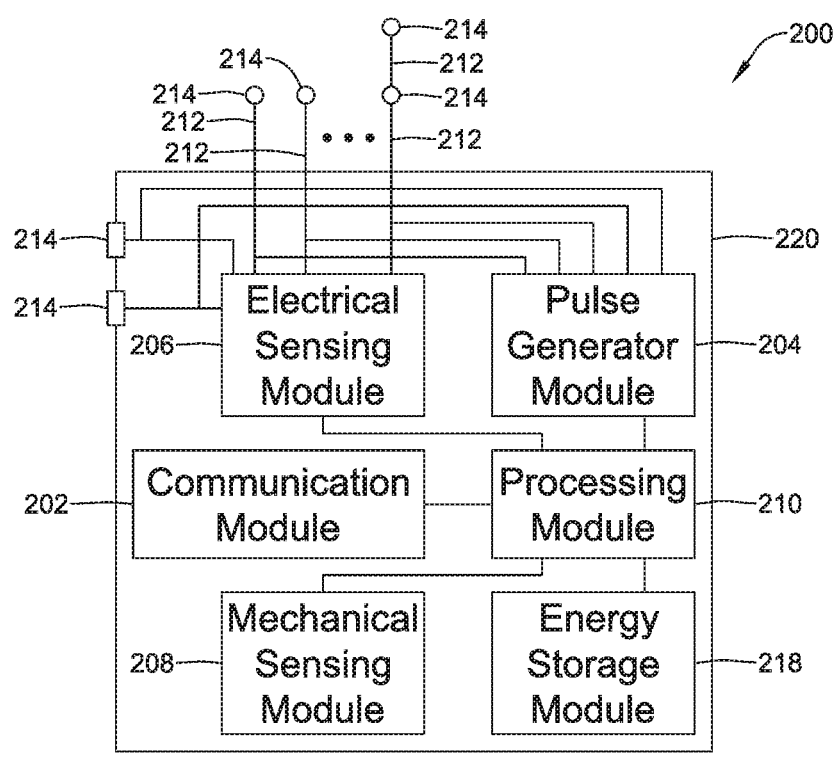
FIG. 2 is a schematic block diagram of an illustrative medical device that may be used in conjunction with the LCP of FIG. 1.

FIG. 2 is a schematic block diagram of an illustrative medical device (MD) 200 that may be used in conjunction with the LCP 100 of FIG. 1. In some cases, The MD 200 may be configured to sense physiological signals and parameters and deliver one or more types of electrical stimulation therapy to tissues of the patient. In the embodiment shown, the MD 200 may include a communication module 202, a pulse generator module 204, an electrical sensing module 206, a mechanical sensing module 208, a processing module 210, and an energy storage module 218. Each of the modules 202, 204, 206, 208, and 210 may be similar to the modules 102, 104, 106, 108, and 110 of the LCP 100. Additionally, the energy storage module 218 may be similar to the energy storage module 112 of LCP 100. However, in some embodiments, the MD 200 may have a larger volume within a housing 220. In such embodiments, the MD 200 may include a larger energy storage module 218 and/or a larger processing module 210 capable of handling more complex operations than the processing module 110 of the LCP 100.

While the MD 200 may be another leadless device such as shown in FIG. 1, in some instances the MD 200 may include leads, such as leads 212. In some instances, the leads 212 may include electrical wires that conduct electrical signals between the electrodes 214 and one or more modules located within the housing 220. In some cases, the leads 212 may be connected to and extend away from the housing 220 of the MD 200. In some embodiments, the leads 212 are implanted on, within, or adjacent to a heart of a patient. The leads 212 may contain one or more electrodes 214 positioned at various locations on the leads 212 and various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to the leads 212. The leads 212 may, in turn, conduct the received electrical cardiac signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical stimulation signals to the cardiac tissue of the patient (either directly or indirectly). The MD 200 may also include one or more electrodes 214 not disposed on a lead 212. For example, one or more electrodes 214 may be connected directly to the housing 220.

The leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, the mechanical sensing module 208 may be in electrical communication with the leads 212 and may receive signals generated from such sensors. In some cases, one or more of these additional sensors may instead be incorporated into or onto the MD 200.

While not required, in some embodiments the MD 200 may be an implantable medical device. In such embodiments, the housing 220 of MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body. In such embodiments, the leads 212 may be implanted at one or more various locations within the patient, such as within the heart of the patient, adjacent to the heart of the patient, adjacent to the spine of the patient, or any other desired location.

In some embodiments, the MD 200 may be an implantable cardiac pacemaker (ICP). In these embodiments, the MD 200 may have one or more leads, for example leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some embodiments, the MD 200 may additionally be configured to provide defibrillation/ cardioversion therapy.

In some instances, the MD 200 may be an implantable cardioverter-defibrillator (ICD). In such embodiments, the MD 200 may include one or more leads implanted within a patient's heart. The MD 200 may also be configured to sense electrical cardiac signals, determine occurrences of tachyarrhythmia's based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, the MD 200 may be a subcutaneous implantable cardioverter-defibrillator (SICD). In embodiments where the MD 200 is an SICD, one of the leads 212 may be a subcutaneously implanted lead. In at least some embodiments where the MD 200 is an SICD, the MD 200 may include only a single lead which is implanted subcutaneously but outside of the chest cavity, however this is not required. In some cases, the lead may be implanted just under the chest cavity.

In some embodiments, the MD 200 may not be an implantable medical device. Rather, the MD 200 may be a device external to the patient's body, and the electrodes 214 may be skin-electrodes that are placed on a patient's body. In such embodiments, the MD 200 may be able to sense surface electrical signals (e.g. electrical cardiac signals that are generated by the heart or electrical signals generated by a device implanted within a patient's body and conducted through the body to the skin). The MD 200 may further be configured to deliver various types of electrical stimulation therapy, including, for example, defibrillation therapy via skin-electrodes 214.

In some cases, implantable medical devices such as the IMD 100 and/or the MD 200 devote a substantial portion of their internal volume to energy storage. It will be appreciated that the life expectancy of an implanted device depends in large part upon the life expectancy of the battery powering the implanted device. Accordingly, there are competing interests in wanting to maximize battery life (and hence device life expectancy) while making implanted devices as small as possible in order to facilitate delivery using various techniques such as trans-catheter delivery as well as to make the implanted devices less intrusive. In some cases, such as for implanted devices intended to be implanted in particular chambers of the heart, there are additional potential size limitations. A device that is too large in diameter may be difficult to deliver while a device that is too long may interfere with the operation of the valve (e.g. interfere with the valve, interfere with blood flow, etc.).

Accordingly, some implanted devices such as but not limited to a leadless cardiac pacemaker (LCP) may be configured to include a rechargeable battery that provides the power needed by the LCP for a limited period of time. Because the rechargeable battery can be recharged in situ, the rechargeable battery can be smaller because it does not have to store sufficient energy to last the entire expected lifetime of the device. Rather, the rechargeable battery only needs to store sufficient energy to power the LCP for a period of time that corresponds to a reasonable recharging schedule. For example, a LCP with a rechargeable battery may undergo a recharging procedure on a daily basis, a weekly basis, a monthly basis, a by-yearly basis, a yearly basis, or any desired schedule, with the recognition that relative size of the rechargeable battery is at least roughly proportional to the interval between rechargings. For example, a relatively small rechargeable battery will take up less space within the LCP but will require more frequent recharging. A relatively large rechargeable battery will take up more space within the LCP but will require less frequent recharging as the larger rechargeable battery can store relatively more chemical energy. In some cases, the battery size may be roughly inversely proportional to the frequency of the impinging energy that is captured and used to recharge the rechargeable battery.

In some cases, an implanted device with a rechargeable battery may be implanted within a patient. In the case of an LCP with a rechargeable battery, the LCP may be implanted within a chamber of the patient's heart. The patient may periodically undergo a recharging procedure in which energy from outside of the patient may be transmitted to the LCP (or other implanted device) within the patient. In some cases, the LCP or other implanted device may include an antenna or other structure that is configured to receive the transmitted energy and the received energy may be used to at least partially recharge the rechargeable battery. It will be appreciated that at least partially recharging the rechargeable battery may, for example, mean recharging the rechargeable battery to capacity. It may mean recharging the rechargeable battery to a charge level that is less than capacity. For example, recharging the rechargeable battery may mean recharging to a charge level that is about 50 percent (%) of capacity, about 60% of capacity, about 70% of capacity, about 80% of capacity, or about 90% of capacity.

Figure 3:
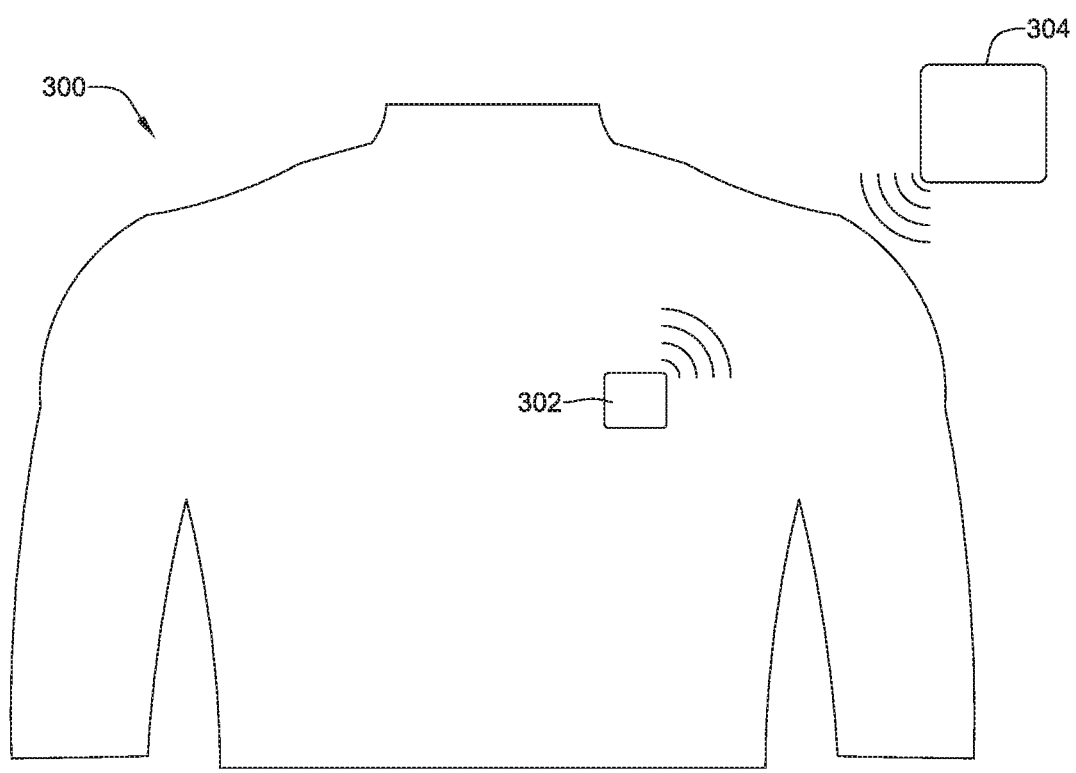
FIG. 3 is a schematic diagram of a patient including a rechargeable implantable medical device system.

FIG. 3 provides a highly schematic illustration of a patient 300 having an implantable device 302 implanted within the patient 300. While the implantable device 302 is shown as being in or near the patient's chest, it will be appreciated that this is merely illustrative, as the implantable device 302, depending on functionality, may be implanted in other locations within the patient 300. A transmitter 304 is shown exterior to the patient 300. In some cases, the transmitter 304 may be configured to transmit electromagnetic (EM) radiative energy that is of a wavelength (or frequency, as wavelength and frequency are related by the numerical speed of light) and intensity that can safety pass into the patient 300 to the implantable device 302 without causing excessive tissue heating or other potentially damaging effects to the patient 300.

The transmitter 304 may take any of a variety of forms. For example, while shown schematically as a box in FIG. 3, the transmitter 304 may be sized and configured for the patient 300 to periodically wear about their neck on a lanyard, which would place the transmitter 304 proximate their chest, at about the same vertical and horizontal position as the implantable device 302 within the patient's chest. In some cases, for example, the transmitter 304 may be built into the back of a chair that the patient 300 would periodically sit in to recharge the implantable device 302. The chair could be in the patient's home, for a daily recharge, for example, or could be at a remote location such as a medical clinic, for a patient 300 having a longer recharge schedule. As another example, the transmitter 304 could be built into a bed such that the transmitter 304 could at least partially recharge the implantable device 302 each evening when the patient 300 sleeps. In some cases, the transmitter 304 could be configured to only transmit once per week, or once per month, for example, depending on the power requirements of the implantable device 302. In some cases, the transmitter 304 and the implantable device 302 may communicate with each other. When so provided, the implantable device 302 may report its current battery recharge level to the transmitter 304, and if the current battery recharge level is below a threshold, the transmitter 304 may transmit power to the implantable device 302.

It will be appreciated that the implantable device 302 may be configured to periodically receive EM energy at a wavelength and intensity that is safe for the patient 300 and that the implantable device 302 may use to recharge a rechargeable battery within the implantable device 302. The EM energy may be received at a rate that exceeds a rate at which power is being drawn from the rechargeable battery and consumed by various components within the implantable device 302.

Figure 4:
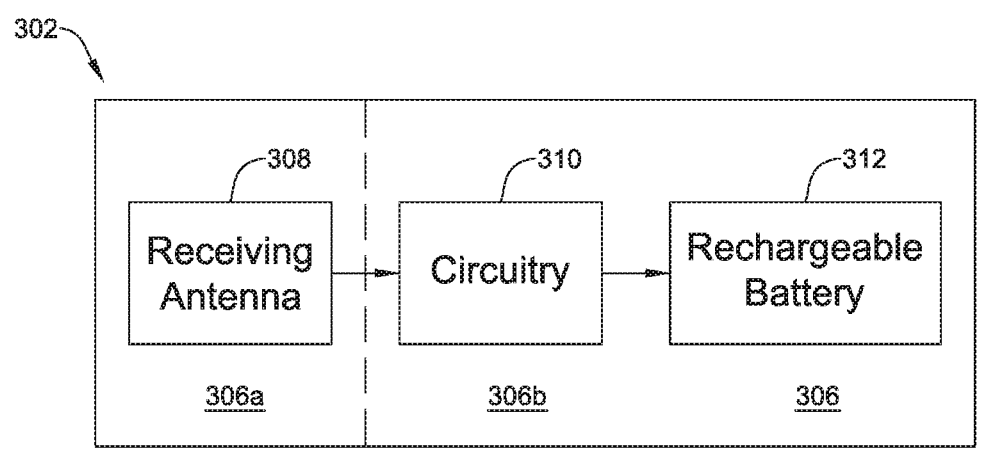
FIG. 4 is a schematic diagram of an illustrative implantable medical device (IMD) according to an example of the disclosure.

FIG. 4 provides an illustrative but non-limiting example of at least some of the internal components within the implantable device 302. In some cases, the implantable device 302 includes a device housing 306. In some cases, the device housing 306 may include at least a portion thereof that is formed of a material that is transparent or at least substantially transparent to the EM energy that is being transmitted from the transmitter 304 to the implantable device 302. In this, "substantially" transparent may be defined, for example, as allowing at least 70%, or at least 80%, at least 90%, or at least 95% of incident energy at a particular wavelength (or range of wavelengths) to pass through the material without being absorbed by the material or blocked by the material. For example, at least a portion of the device housing 306, or even all of the device housing 306, may be made of a material such as glass or a ceramic. To illustrate, perhaps a first portion 306a of the device housing 306, which overlays a receiving antenna 308, may be made of a material that is transparent or at least substantially transparent to the EM energy that is being transmitted from the transmitter 304 while a second portion 306b of the device housing 306, which does not overlay the receiving antenna 308, may be made of other materials such as but not limited to metals which could otherwise interference with EM energy transmitted from the transmitter 304 reaching the receiving antenna 308. In some cases, both the first portion 306a and the second portion 306b may be made of a material that is transparent or at least substantially transparent to the EM energy that is being transmitted from the transmitter 304.

The receiving antenna 308 may be any of a variety of different types of antennas. In some cases, the receiving antenna 308 may be a planar antenna, which in some cases is then conformed to a non-planar surface. In some cases, a planar antenna may be an antenna that is printed or deposited onto a planar surface, or perhaps etched into a planar surface. In some instances, depending on how the receiving antenna 308 is incorporated into the implantable device 302, the receiving antenna 308 may be considered as being a three-dimensional analog of a planar antenna (e.g. conformed to a non-planar shape). Illustrative but non-limiting examples of planar antennas include path antennas, slot antennas, ring antennas, spiral antennas, bow-tie antennas, TSA (Vivaldi) antennas, LPDA antennas, leaky-wave antennas and quasi-yagi antennas. In some cases, the antenna may include a resonator structure that helps to make the antenna more efficient and/or to increase an effective electrical length of the antenna such that the antenna may be made physically smaller.

EM energy that is transmitted from the transmitter 304 may be captured by the receiving antenna 308 and provided to a circuitry 310. In some cases, the circuitry 310 may be configured to convert the received EM energy into a form that may be used to recharge a rechargeable battery 312. In some cases, the circuitry 310 may also provide other functionality to the implantable device 302. For example, if the implantable device 302 is an LCP, the circuitry 310 may, in addition to recharging the rechargeable battery 312, also provide sense functions, pace functions, or sense and pace functions. In some instances, the circuitry 310 only functions to recharge the rechargeable battery 312, and the implantable device 302 may include other circuitry (not shown) to provide whichever other functions are ascribed to the implantable device 302.

When considering the electromagnetic regions around a transmitting antenna, there are three categories; namely, (1) reactive near-field; (2) radiated near-field and (3) radiated far-field. "Inductive" charging systems operate in the reactive near-field region. In inductive power systems, power is typically transferred over short distances by magnetic fields using inductive coupling between coils of wire, or by electric fields using capacitive coupling between electrodes. In radiative power systems (e.g. radiated near-field and radiated far-field), power is typically transmitted by beams of electromagnetic (EM) energy. Radiative power systems can often transport energy for longer distances, but the ability of a receiving antenna to capture sufficient energy can be challenging, particular for applications where the size of the receiving antenna is limited.

In some cases, the transmitter 304 and implantable medical device 302 may operate at or above about 400 MHz within the patient's body. When so provided, the system does not operate in the reactive near-field (as in inductive charging system), but rather operates in either the radiated near-field or radiated far-field regions (depending on the placement of the implanted device and band of usage). For example, when the EM energy is transmitted at 400 MHz, the system is in the radiated near-field region and at 2.45 GHz the system is in the radiated far-field region. In some cases, the present system may operate at a frequency that is between, for example, about 400 MHz and 3 GHz. In some cases, more than one frequency within this range may be used simultaneously and/or sequentially. In some cases, multiple implanted devices may be simultaneously or sequentially charged using both the radiated near-field and radiated far-field regions.

The rechargeable battery 312 may be any type of rechargeable battery 312, and may take a three dimensional shape that facilitates incorporation of the rechargeable battery 312 into the device housing 304. In some cases, the rechargeable battery 312 may instead be a supercapacitor. As will be appreciated, in some cases the device housing 304 may have a cylindrical or substantially cylindrical shape, in which case a rechargeable battery 312 having an cylindrical or annular profile, such as a button battery or an elongated (in height) battery having a substantially cylindrical shape, may be useful. It is recognized that there are possible tradeoffs in rechargeable battery shape and dimensions relative to performance, so these issues should be considered in designing the rechargeable battery 312 for a particular use. While FIG. 4 schematically shows a single rechargeable battery 312, in some cases there may be two, three or more distinct rechargeable batteries 312, each electrically coupled with the circuitry 310. For example, in some cases there may be performance advantages in having multiple rechargeable batteries 312. In some instances, there may be packaging advantages to having multiple (and smaller) rechargeable batteries 312.

Figure 5:
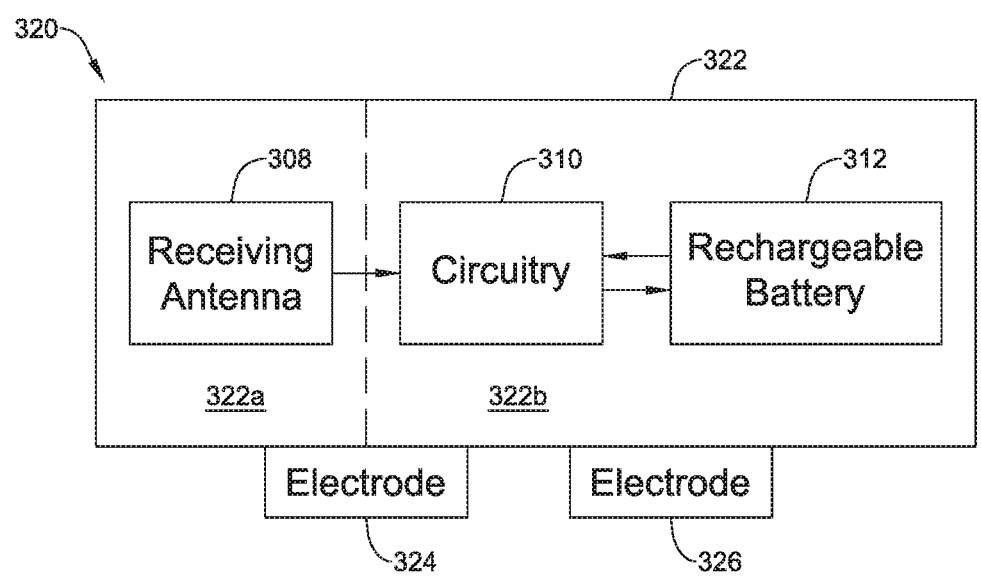
FIG. 5 is a schematic diagram of another illustrative IMD according to an example of the disclosure.

FIG. 5 provides a schematic view of an IMD 320 that may be configured to be implanted within a patient such as the patient 300 (FIG. 3). The illustrative IMD 320 includes a housing 322 that is substantially transparent to EM energy such as radiative EM energy along at least part of its length. For example, in some cases, a first portion 322a of the housing 322 may be substantially transparent to radiative EM energy while a second portion 322b of the housing 320 may be less transparent to radiative EM energy. In some cases, the second portion 322b of the housing 320 may also be substantially transparent to radiative EM energy. In some cases, at least the first portion 322a of the housing 320 may be ceramic or glass. Circuitry 310 may be disposed within the housing 320. In some cases, as described with respect to FIG. 4, the circuitry 310 may be mono-functional, meaning its only function is for recharging, or the circuitry 310 may be multi-functional, meaning that the circuitry 310 has additional functionality beyond recharging.

In some cases, a first electrode 324 and a second electrode 326 may be exposed external to the housing 320 and may be operably coupled to the circuitry 310. While two electrodes are illustrated, it will be appreciated that in some instances the IMD 320 may include three, four or more distinct electrodes. Depending on the intended functionality of the IMD 320, the first electrode 324 and the second electrode 326, in combination, may be used for sensing and/or pacing the patient's heart. In some instances, for example, the IMD 320 may be a leadless cardiac pacemaker (LCP), an implantable monitoring device or an implantable sensor. In some cases, the first electrode 324 and the second electrode 326 may, in combination, be used for communicating with other implanted devices and/or with external devices. In some cases, communication with other implanted devices may include conductive communication, but this is not required. Rechargeable battery 312 may be disposed within the housing 320 and may be configured to power the IMD 320, including the circuitry 310.

Receiving antenna 308 may be disposed within the housing 320 and may be configured to receive transmitted radiative EM energy through the housing 320, such as through the first portion 322a of the housing 320 that is substantially transparent to radiative EM energy. The circuitry 310 may be operably coupled with the receiving antenna 308 and the rechargeable battery 312. In some cases, the circuitry 310 may be configured to charge the rechargeable battery 312 using the radiative EM energy received by the receiving antenna 308. In some cases, the receiving antenna 308 may be configured to receive sufficient radiative EM energy from a wavelength band of radiative EM energy transmitted from outside the patient 300 (FIG. 3) to recharge the rechargeable battery 312 at a rate faster than the rechargeable battery 312 is depleted by powering the IMD 320 when the wavelength band of radiative EM energy is transmitted at an intensity that does not cause heat damage to the patient 300. In some cases, the housing 320 has a substantially cylindrical profile and the receiving antenna 308 includes a planar antenna that has been conformed to the substantially cylindrical profile of an inner surface of an inner cavity defined by the housing 320.

Figure 6:
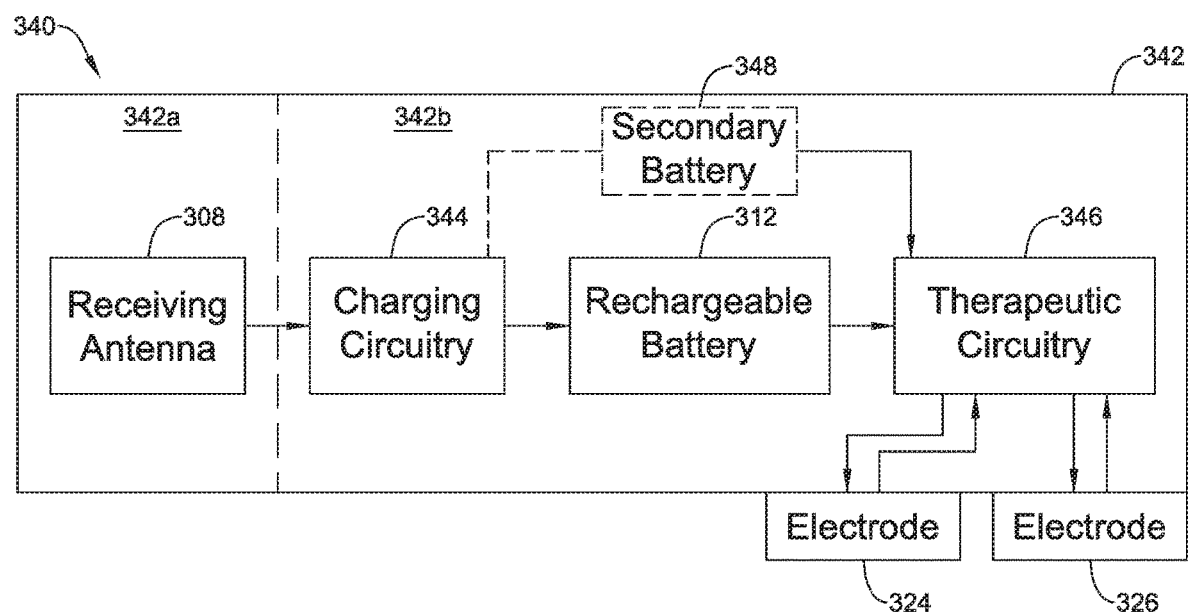
FIG. 6 is a schematic diagram of another IMD according to an example of the disclosure.

FIG. 6 provides a schematic view of an IMD 340 that may be configured to be implanted within a patient such as the patient 300 (FIG. 3). The illustrative IMD 340 includes a housing 342 that may be configured for trans-catheter deployment. In some cases, this means that the housing 342 has overall dimensions that enable the IMD 340 to fit within a catheter or similar device for delivering the IMD 340 via a vascular approach. In some cases, the housing 342 may have an overall length of perhaps about five centimeters or less, or perhaps about three centimeters or less, and/or an overall width of perhaps about 2 centimeters or less, or perhaps about 1 centimeter or less. In some cases, for example, the housing 342 may also be substantially transparent to EM energy such as radiative EM energy along at least part of its length. For example, in some cases, a first portion 342a of the housing 342 may be substantially transparent to radiative EM energy while a second portion 342b of the housing 342 may be less transparent to radiative EM energy. In some cases, the second portion 342b of the housing 342 may also be substantially transparent to radiative EM energy. In some cases, at least the first portion 342a of the housing 342 may be ceramic or glass. In some cases, the housing 342 (or portions thereof) may be a ceramic housing, a glass housing or a polymeric housing.

While the illustrative IMD 320 (FIG. 5) included a single circuitry 310, which could be mono-functional or multi-functional, in some cases the IMD 340 (FIG. 6) includes charging circuitry 344 and therapeutic circuitry 346. In some cases, the charging circuitry 344 and the therapeutic circuitry 346 may be located on distinct circuit boards or be manifested within distinct integrated circuits (ICs). In some cases, the charging circuitry 344 and the therapeutic circuitry 346, while shown as distinct elements, may be combined within a single IC or on a single circuit board. The charging circuitry 344 may be operably coupled with the receiving antenna 308 and the rechargeable battery 312, and may be configured to use the radiative EM energy received by the receiving antenna 308 to charge the rechargeable battery 312.

In some cases, the IMD 340 may include a secondary battery 348 that is disposed within the housing 342 and that is operably coupled to the therapeutic circuitry 346. In some cases, the secondary battery 348 may function as a backup battery to the rechargeable battery 312. In some instances, the secondary battery 348 may also be a rechargeable battery and thus may also be operably coupled with the charging circuitry 344. In some cases, the secondary battery 348 may be a non-rechargeable battery.

In some cases, the therapeutic circuitry 346 may be operatively coupled to the first electrode 324 and the second electrode 326. While two electrodes are illustrated, it will be appreciated that in some instances the IMD 340 may include three, four or more distinct electrodes. In some instances, the therapeutic circuitry 346 may be configured to sense one or more signals via the electrodes 324, 326 (or additional electrodes) and/or to stimulate tissue via the electrodes 324, 326. In some cases, the therapeutic circuitry 346 may pace, or stimulate tissue, at least partly in response to the one or more sensed signals. In some cases, the first electrode 324 and the second electrode 326 may, in combination, be used for communicating with other implanted devices and/or with external devices. In some cases, communication with other implanted devices may include conductive communication, but this is not required in all cases.

Figure 7:
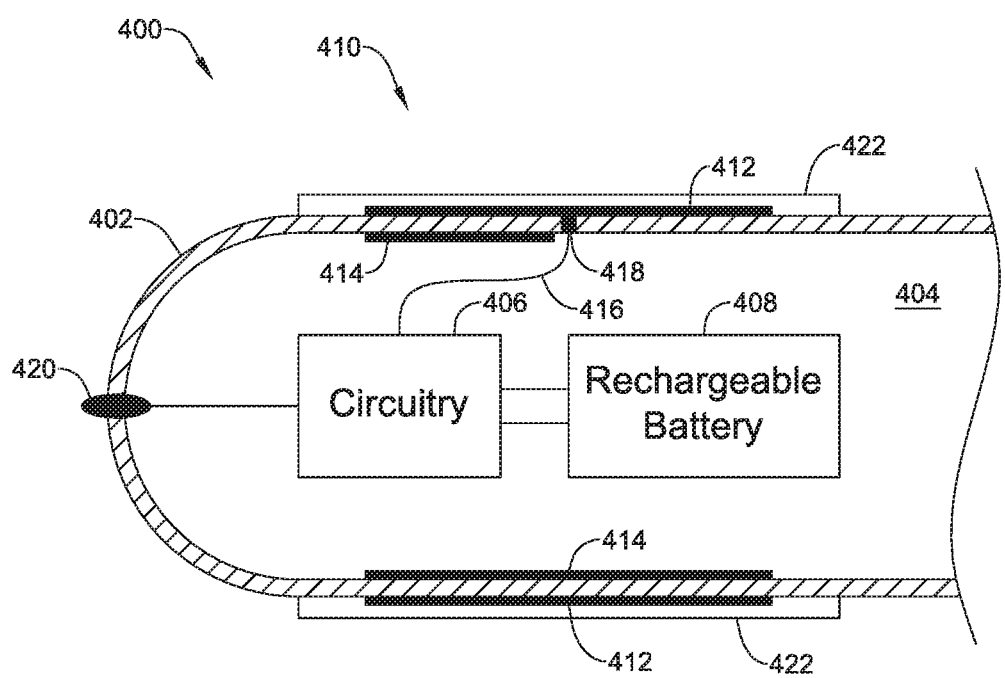
FIG. 7 is a partial cross-sectional side view of an LCP according to an example of the disclosure.

FIG. 7 is a schematic cross-sectional side view of an illustrative LCP 400 having a rechargeable battery. The illustrative LCP 400 has a housing 402 that is formed of a ceramic material, a glass material or perhaps a polymeric material. It will be appreciated, therefore, that the housing 402 is at least substantially transparent to radiative EM energy that is incident upon the LCP 400. The housing 402 defines an interior volume 404 that houses a variety of different components, including but not limited to circuitry 406 and a rechargeable battery 408. In some cases the circuitry 406 may be limited to recharging the rechargeable battery 408. In some instances, the circuitry 406 may also have additional functionality such as sensing and/or pacing, although in some cases the LCP 400 may include additional circuitry for additional functionality. In some cases, the circuitry 406 is operably coupled with a first electrode 420 and one or more other electrodes (not shown).

A receiving antenna 410 is operably coupled to the circuitry 406. In some cases, as illustrated, the housing 402 itself may form at least one or more layers of the receiving antenna 410. In some cases, the receiving antenna 410 includes an outer metal layer 412 and an inner metal layer 414, connected by a via 416 extending through an aperture 418 in the housing 402 wall. While the outer metal layer 412 and the inner metal layer 414 are schematically illustrated as simple layers, it will be appreciated that in some cases the outer metal layer 412 and/or the inner metal layer 414 may include patterns within the metal. The outer metal layer 412 and/or the inner metal layer 414 may, for example, be formed by etching away portions of a base metal layer. In some cases, the outer metal layer 412 and/or the inner metal layer 414 may be formed via a deposition process. In some cases, the ceramic or other material forming the housing 402 may function as a dielectric layer between the outer metal layer 412 and the inner metal layer 414.

In some cases, a biocompatible polymeric layer 422 may cover the outer metal layer 412. The biocompatible polymeric layer 422 may, for example, be formed of a polyimide or Parylene. In some cases, depending on the exact material used to form the housing 402, and whether the exact material is biocompatible, a polymeric coating (not shown) may cover essentially all of the outer surface of the housing 402 in order to improve biocompatibility. In some instances, particularly if the housing 402 is formed of a material having any porosity, a polymeric covering may help to reduce porosity.

In some cases, and as shown in FIG. 7, the receiving antenna 410 may be built right into the housing 402 of the LCP 400. In some cases, however, the receiving antenna may be formed in or on a first structure that can subsequently be inserted into or advanced over a device housing. For example, FIG. 8 shows a sleeve insert that can be inserted into a device housing, and FIG. 9 shows an outer sleeve that can be disposed over a device housing.

Figure 8:
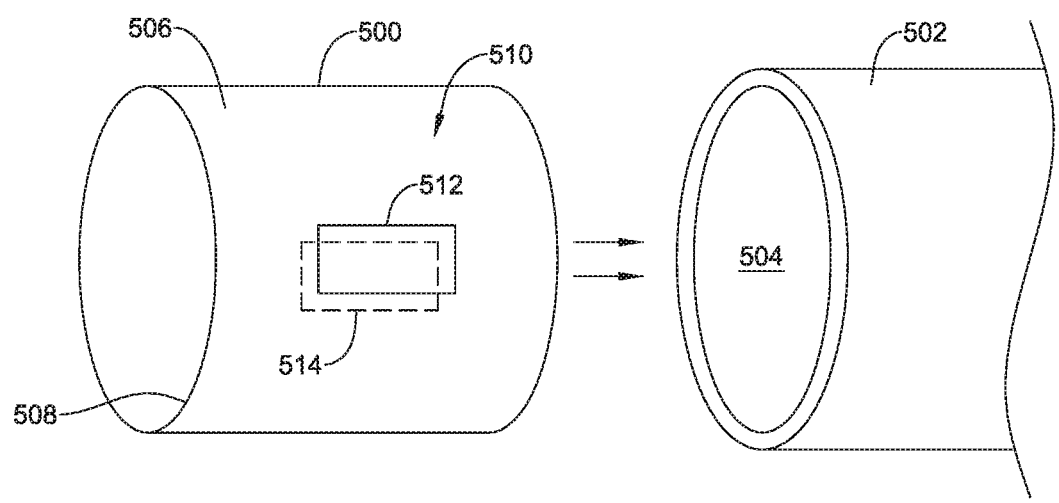
FIG. 8 is a schematic diagram of an illustrative IMD with an inner sleeve insert.

More specifically, FIG. 8 shows a sleeve insert 500 that is configured to be insertable into a device housing 502. The device housing 502 includes an elongated cavity 504 that is configured to accommodate the sleeve insert 500 therein. While the elongated cavity 504 is illustrated as generally being an entire interior space of the device housing 502, it will be appreciated that in some cases the interior of the device housing 502 may be divided into compartments, and the elongated cavity 504 may be one of those compartments. The sleeve insert 500 may be considered as having an outer surface 506 and an inner surface 508. A receiving antenna 510 may be built into the sleeve insert 500. In some cases, the receiving antenna 510 includes a first metal pattern 512 that is formed on the outer surface 506 and a second metal pattern 514 that is formed on the inner surface 508. The material forming the sleeve insert 500 may, for example, include a dielectric layer and may itself form part of the receiving antenna 510. In some cases, the first metal pattern 512 and the second metal layer 514 may form an antenna with a resonator. The device housing 502 may be at least substantially transparent to radiative EM energy to allow the radiative EM energy to reach the receiving antenna 510.

Figure 9:
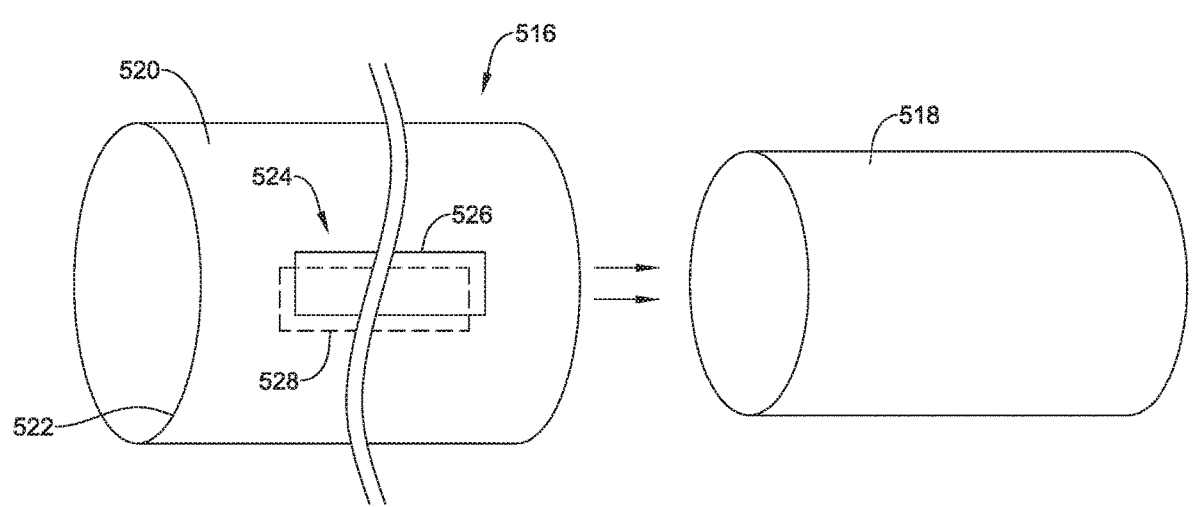
FIG. 9 is a schematic diagram of an illustrative IMD with an outer sleeve.

FIG. 9 shows an outer sleeve 516 that is configured to fit over a device housing 518. In some cases, the outer sleeve 516 may be considered as having an outer surface 520 and an inner surface 522. The outer sleeve 516 may include a receiving antenna 524 that is built into the outer sleeve 516. In some cases, for example, the receiving antenna 524 may include a first metal pattern 526 that is formed on the outer surface 520 and a second metal pattern 528 that is formed on the inner surface 522. The material forming the outer sleeve 516 may, for example, include a dielectric layer and may itself form part of the receiving antenna 524. In some cases, the first metal pattern 526 and the second metal layer 528 may form an antenna with a resonator. In this embodiment, the device housing 518 need not be substantially transparent to radiative EM energy since the radiative EM energy need not travel through the device housing 518 to reach the receiving antenna 524.

Figure 10:
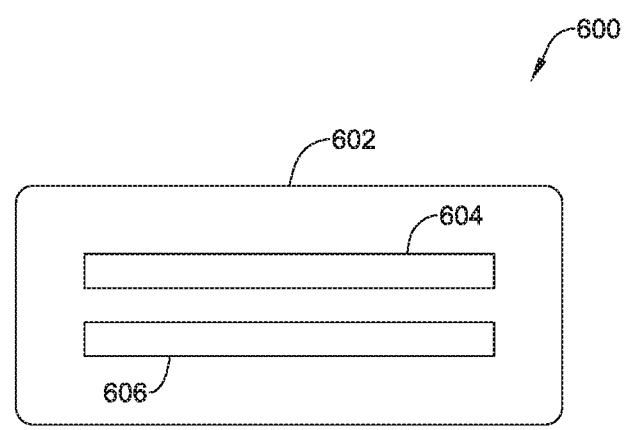
FIGS. 10-14 are schematic diagrams showing example receiving antenna configurations.
Figure 11:
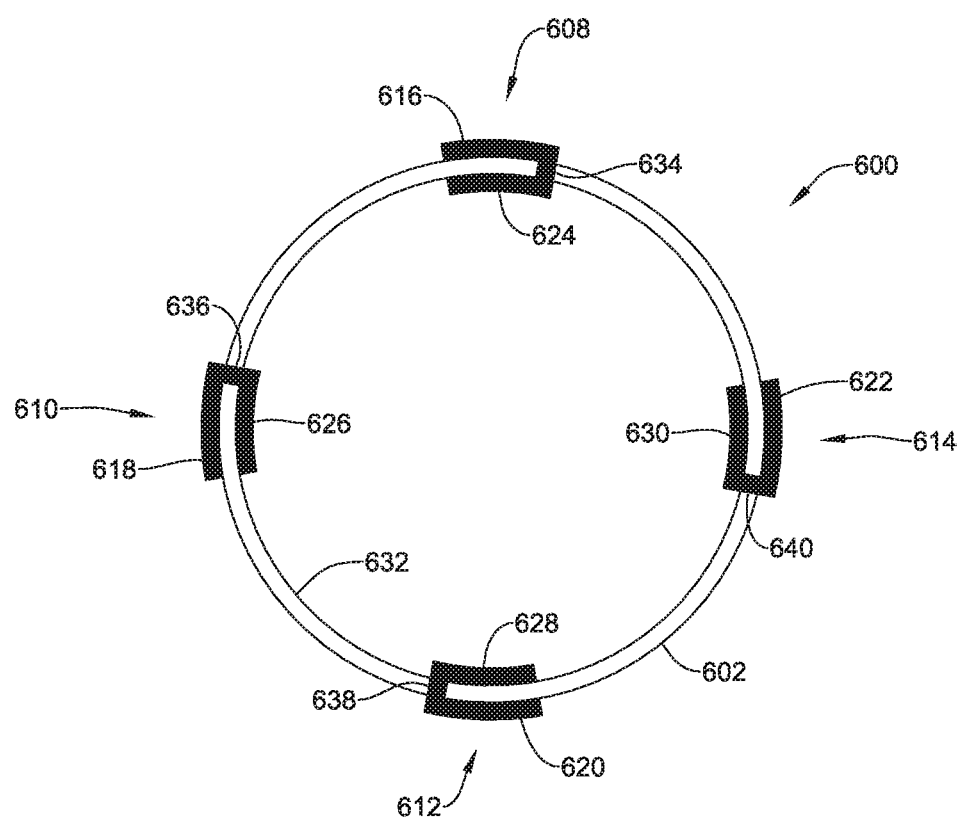
Figure 12:
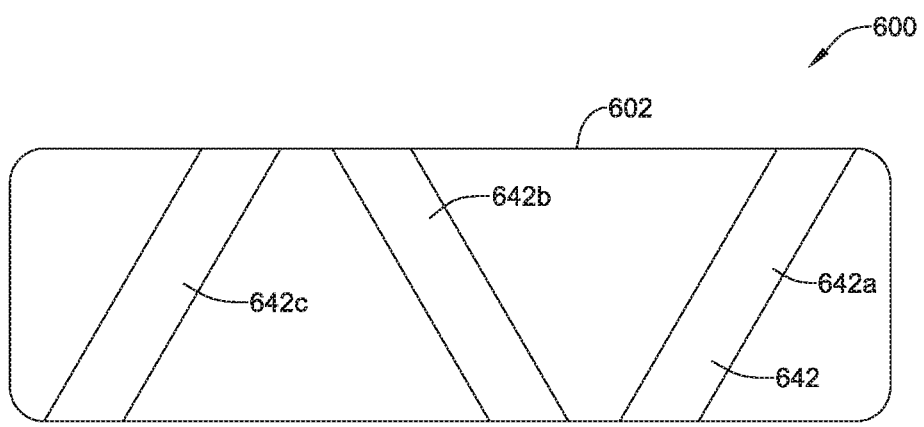

FIGS. 10 through 12 provide illustrative but non-limiting examples of receiving antenna patterns. It will be appreciated that these patterns (and others) may be built directly into a device housing, as shown for example in the LCP 400 of FIG. 7. In some cases, these patterns (and others) may be used in building a sleeve insert such as the sleeve insert 500 (FIG. 8). In some instances, these patterns (and others) may be used in building an outer sleeve such as the outer sleeve 516. FIGS. 10-12 illustrate a cylindrical form 600 that may, for example, represent a sleeve insert or an outer sleeve, or perhaps a device housing. While shown as a cylinder, it will be appreciated that the cylindrical form 600 may take any desired shape, size or configuration.

The cylindrical form 600 includes an outer surface 602. In FIG. 10, a first receiving antenna 604 and a second receiving antenna 606 are shown disposed relative to the outer surface 602. The receiving antenna 604 and the receiving antenna 606 may, for example, be formed entirely on the outer surface 602. In some cases, the receiving antenna 604 and the receiving antenna 606 may be formed with components on the outer surface 602 and components interior to the cylindrical form 600 (e.g. antenna with a resonator).

While two receiving antennae 604 and 606 are shown, the device may include any number of receiving antennae. FIG. 11, for example, is a schematic cross-sectional view showing a total of four receiving antennae 608, 610, 612, 614, with each receiving antenna constructed with a first metal pattern 616, 618, 620, 622 disposed on the outer surface 602 and a corresponding second metal pattern 624, 626, 628, 630 disposed on an inner surface 632, with vias 634, 636, 638, 640 extending between the first metal pattern 616, 618, 620, 622 and the second metal pattern 624, 626, 628, 630.

FIG. 12 illustrates a receiving antenna 642 that is laid out in a helical or spiral pattern relative to the outer surface 602. The receiving antenna 642 may, for example, be formed entirely on the outer surface 602. In some cases, the receiving antenna 524 may be formed with components on the outer surface 602 and components interior to the cylindrical form 600. While indicated as a single helical receiving antenna 642, in some cases the receiving antenna 642 may instead have distinct segments, such as a segment 642a, a segment 642b and a segment 642c.

Figure 13:
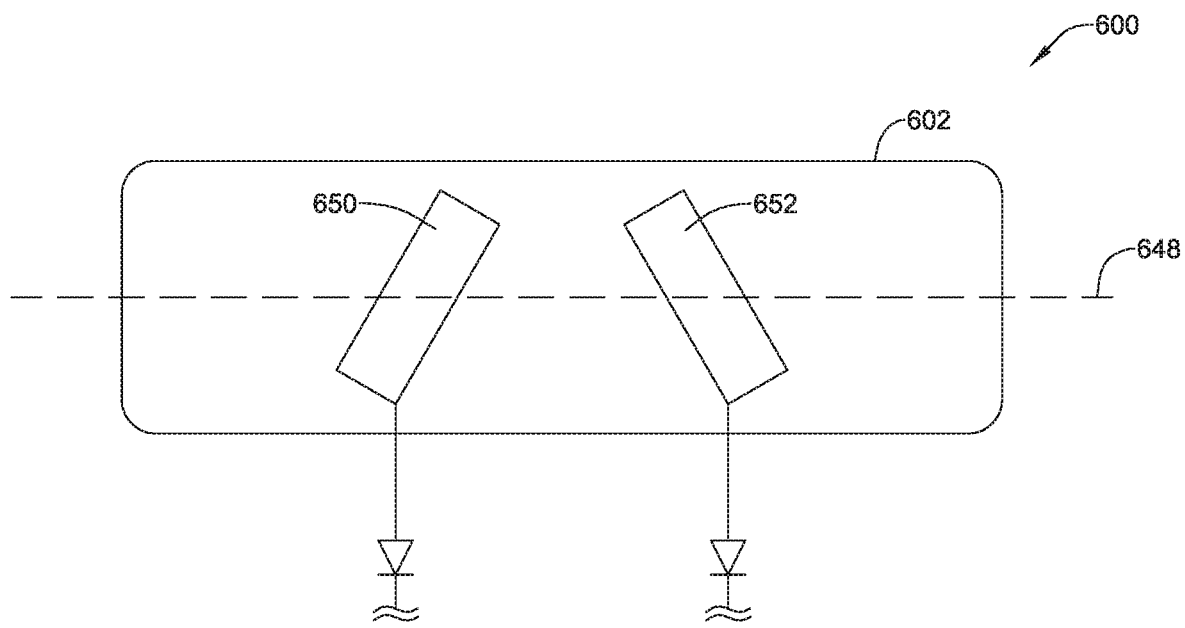
Figure 14:
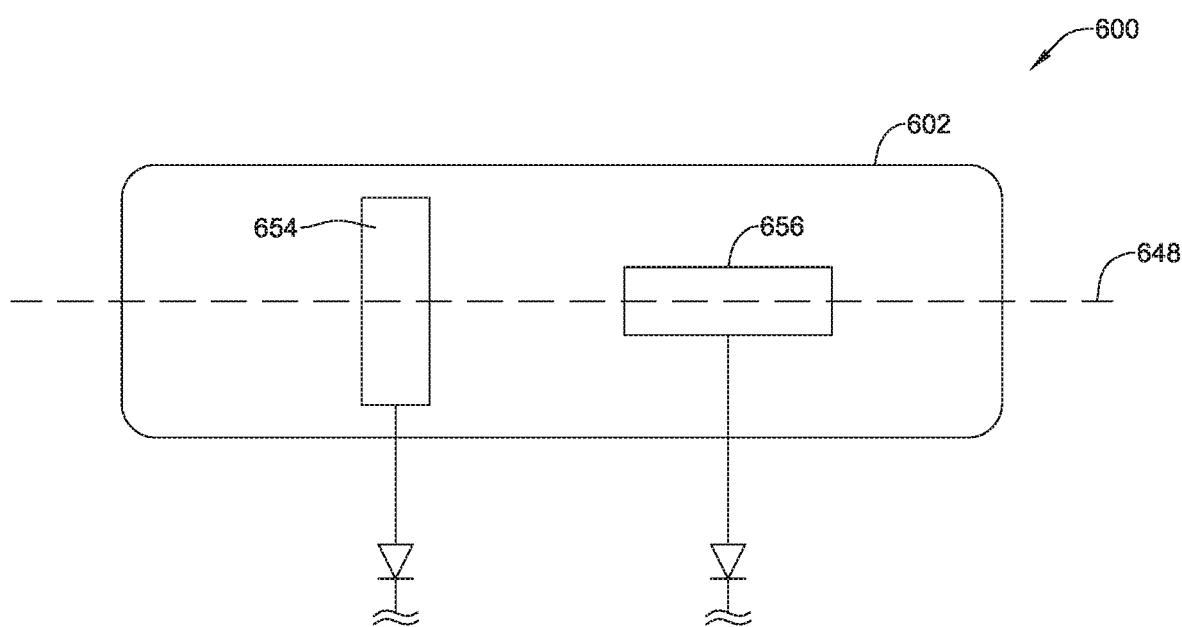

It will be appreciated that in some cases, an antenna such as a receiving antenna may have a null such as a spatial null and/or a frequency null. A spatial null indicates a direction from which no signal or very little signal may be received. A frequency null indicates a particular frequency or range of frequencies for which no signal or very little signal may be received. In some cases, if a device such as an implantable device includes two or more receiving antennae, it will be appreciated that each antenna may have a spatial null. There may be advantages to laying out the two or more receiving antenna such that the spatial nulls do not align in space. This may be particularly useful in an implantable device, in which the exact implanted orientation of the device is uncertain and/or may change with time. In many cases, particularly if the implantable device is planted in or on the heart, the device is constant moving. FIGS. 13 and 14 provide several illustrative but non-limiting examples of how antennae may be laid out in order to intentionally miss-align their respective spatial nulls.

In FIG. 13, a first receiving antenna 650 is laid out relative to the outer surface 602 of the cylindrical form 600, oriented at a first angle relative to a longitudinal axis 648. A second receiving antenna 652 is laid out relative to the outer surface 602, oriented at a second angle relative to the longitudinal axis 648, with the first angle being different from the second angle. In FIG. 14, a first receiving antenna 654 is laid out relative to the outer surface 602, oriented roughly perpendicular to the longitudinal axis 648. A second receiving antenna 656 is laid out relative to the outer surface 602, oriented roughly parallel with the longitudinal axis 648. It will be appreciated that one or more of the receiving antennae 650, 652, 654, 656 may, for example, be formed entirely on the outer surface 602. In some cases, one or more of the receiving antennae 650, 652, 654, 656 may be formed with components on the outer surface 602 and components interior to the cylindrical form 600. It will also be appreciated that the angles shown in FIGS. 13 and 14 are merely illustrative.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An implantable medical device (IMD) configured to be implanted within a patient, the IMD comprising:
 a housing having a wall that defines an elongated cavity, the housing configured for trans-catheter deployment;
 a plurality of electrodes exposed external to the housing;
 therapeutic circuitry disposed within the elongated cavity of the housing, the therapeutic circuitry operatively coupled to the plurality of electrodes and configured to sense one or more signals via one or more of the plurality of electrodes and/or to stimulate tissue via one or more of the plurality of electrodes;
 a rechargeable power source disposed within the elongated cavity of the housing and configured to power the therapeutic circuitry;
 a receiving antenna disposed relative to the housing and configured to receive transmitted radiative Electro-Magnetic (EM) energy through the patient's body that is transmitted at a frequency between about 400 MHz and about 3 GHz, the receiving antenna comprising a first metal pattern disposed on an inner curved surface of an elongate annular dielectric sleeve and a second metal pattern disposed on an outer curved surface of the elongate annular dielectric sleeve, wherein the elongate annular dielectric sleeve is coaxially aligned with and extends longitudinally along the housing, is shaped to conform along the wall of the housing, and encircles at least a portion of at least one of the therapeutic circuitry and the rechargeable power source, and wherein the first metal pattern, the second metal pattern and the elongate annular dielectric sleeve together form the receiving antenna; and
 charging circuitry operably coupled with the receiving antenna and the rechargeable power source, the charging circuitry configured to use the radiative EM energy received via the receiving antenna to charge the rechargeable power source.

2. The IMD of claim 1, further comprising a secondary battery disposed within the housing and operatively coupled to the therapeutic circuitry, the secondary battery functioning as a backup battery to the rechargeable power source.

3. The IMD of claim 2, wherein the secondary battery is a non-rechargeable battery.

4. The IMD of claim 1, wherein the IMD comprises a leadless cardiac pacemaker (LCP).

5. The IMD of claim 1, wherein the housing is substantially transparent to radiative EM energy.

6. The IMD of claim 5, wherein the housing comprises a ceramic housing, a glass housing, or a polymeric housing.

7. The IMD of claim 5, wherein the elongate annular dielectric sleeve is substantially cylindrical and is inserted into the elongated cavity of the housing of the IMD, conforms along an inner surface of the wall of the housing, and encircles at least a portion of at least one of the therapeutic circuitry and the rechargeable power source.

8. The IMD of claim 1, wherein the elongate annular dielectric sleeve is substantially cylindrical and fits over the outside of the housing, conforms to an outer surface of the wall of the housing, and is secured relative to the housing of the IMD.

9. The IMD of claim 1, wherein the at least one of the plurality of electrodes forms part of the receiving antenna.

10. An implantable medical device (IMD) configured to be implanted within a patient, the IMD comprising:
 an elongated housing that is substantially transparent to radiative Electro-Magnetic (EM) energy along at least part of its length;
 circuitry disposed within the housing;
 a plurality of electrodes exposed external to the housing and operatively coupled to the circuitry;
 a rechargeable power source disposed within the housing and configured to power the IMD including the circuitry;
 a receiving antenna disposed within the housing and configured to receive transmitted radiative EM energy through the at least part of the housing that is substantially transparent to radiative EM energy, the receiving antenna includes a first metal pattern that is formed on an inner surface of an elongate annular sleeve and a second metal pattern that is formed on an outer surface of the elongated annular sleeve, the elongate annular sleeve wrapping around at least a portion of at least one of the circuitry and the rechargeable power source; and
 the circuitry operably coupled with the receiving antenna and the rechargeable power source, the circuitry configured to use the radiative EM energy received via the receiving antenna to charge the rechargeable power source;
 wherein at least a portion of the housing has a substantially cylindrical profile and the receiving antenna also has a substantially cylindrical profile.

11. The IMD of claim 10, wherein the IMD comprises a leadless cardiac pacemaker (LCP).

12. The IMD of claim 10, wherein the IMD comprises an implantable monitoring device.

13. The IMD of claim 10, wherein the IMD comprises an implantable sensor.

14. The IMD of claim 10, wherein the receiving antenna comprises a first receiving antenna having a first null and a second receiving antenna having a second null offset from the first null.

15. The IMD of claim 10, wherein the housing comprises ceramic.

16. The IMD of claim 10, wherein the housing comprises glass.

17. The IMD of claim 10, wherein the receiving antenna is configured to receive sufficient radiative EM energy from a wavelength band of radiative EM energy transmitted from outside the patient to recharge the rechargeable power source at a rate faster than the rechargeable power source is depleted by powering the IMD when the wavelength band of radiative EM energy is transmitted at an intensity that does not cause heat damage to the patient.

18. An implantable medical device (IMD) configured to be implanted within a patient, the IMD comprising:

a housing having an elongated cavity, the housing forming one or more layers of a multiple layer receiving antenna, wherein the multiple layer receiving antenna is configured to receive transmitted radiative Electro-Magnetic (EM) energy through the patient's body;

a plurality of electrodes exposed external to the housing;

circuitry disposed within the elongated cavity of the housing, the circuitry operatively coupled to the plurality of electrodes and configured to sense one or more signals via one or more of the plurality of electrodes and/or to stimulate tissue via one or more of the plurality of electrodes;

a rechargeable power source disposed within the elongated cavity of the housing and configured to power the circuitry;

charging circuitry disposed within the elongated cavity of the housing and operably coupled with the multiple layer receiving antenna and the rechargeable power source, the charging circuitry configured to use the radiative EM energy received via the multiple layer receiving antenna to charge the rechargeable power source; and wherein the multiple layer receiving antenna at least partially surrounds the circuitry, the rechargeable power source and/or the charging circuitry.

* * * * *